United States Patent
Sherry et al.

(10) Patent No.: US 6,748,953 B2
(45) Date of Patent: Jun. 15, 2004

(54) METHOD FOR THERMAL TREATMENT OF TYPE II ENDOLEAKS IN ARTERIAL ANEURYSMS

(75) Inventors: John Sherry, Needham, MA (US); David J. Sauvageau, Methuen, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/170,043

(22) Filed: Jun. 11, 2002

(65) Prior Publication Data

US 2003/0229340 A1 Dec. 11, 2003

(51) Int. Cl.$^7$ ............................................ A61B 19/00
(52) U.S. Cl. ............................ 128/898; 606/28; 606/49
(58) Field of Search ........................ 128/898; 606/27, 606/28, 41, 42, 48–50; 604/21, 22, 14

(56) References Cited

U.S. PATENT DOCUMENTS

| | | | | |
|---|---|---|---|---|
| 4,581,017 A | * | 4/1986 | Sahota | 604/101.01 |
| 5,087,247 A | | 2/1992 | Horn et al. | 604/98 |
| 5,098,429 A | * | 3/1992 | Sterzer | 606/28 |
| 5,114,423 A | * | 5/1992 | Kasprzyk et al. | 606/27 |
| 5,277,201 A | * | 1/1994 | Stern | 607/98 |
| 5,405,322 A | | 4/1995 | Lennox et al. | 604/53 |
| 5,458,575 A | | 10/1995 | Wang | 604/101 |
| 5,591,224 A | * | 1/1997 | Schwartz et al. | 623/1.22 |
| 5,681,308 A | * | 10/1997 | Edwards et al. | 606/41 |
| 6,039,749 A | | 3/2000 | Marin et al. | 606/198 |
| 6,425,877 B1 | * | 7/2002 | Edwards | 604/21 |
| 2002/0026217 A1 | * | 2/2002 | Baker et al. | 606/223 |
| 2003/0014075 A1 | * | 1/2003 | Rosenbluth et al. | 606/213 |

* cited by examiner

Primary Examiner—Michael Peffley
(74) Attorney, Agent, or Firm—Bingham McCutchen LLP

(57) ABSTRACT

A method and apparatus that facilitates the prevention of type II endoleaks in stent-graft treated arterial aneurysmal sacs comprising a catheter having an elongate tubular body with a balloon or wire mesh basket attached to the body adjacent its distal end. The balloon preferably comprising a plurality of energy conducting elements attached thereto for transmitting RF energy to tissue to be treated. In operation, the catheter is inserted into the femoral artery of a patient and then advanced through the femoral artery into the aorta until the balloon or basket is positioned within an aneurysmal sac. Once in place, the balloon or basket is expanded to compress the clot material within the aneurysmal sack under a pressure in the range of about 2–5 atmospheres. While compressed, the clot material is then heated by transmitting RF energy to the wire basket or the conducting elements on the balloon until the clot material is cauterized and collateral blood flow channels in the clot material are occluded. The balloon or basket is then returned to an unexpanded state and the catheter is removed from the aorta. Once the catheter is removed, a stent-graft may be placed within the aorta in accordance with conventional procedures.

19 Claims, 5 Drawing Sheets

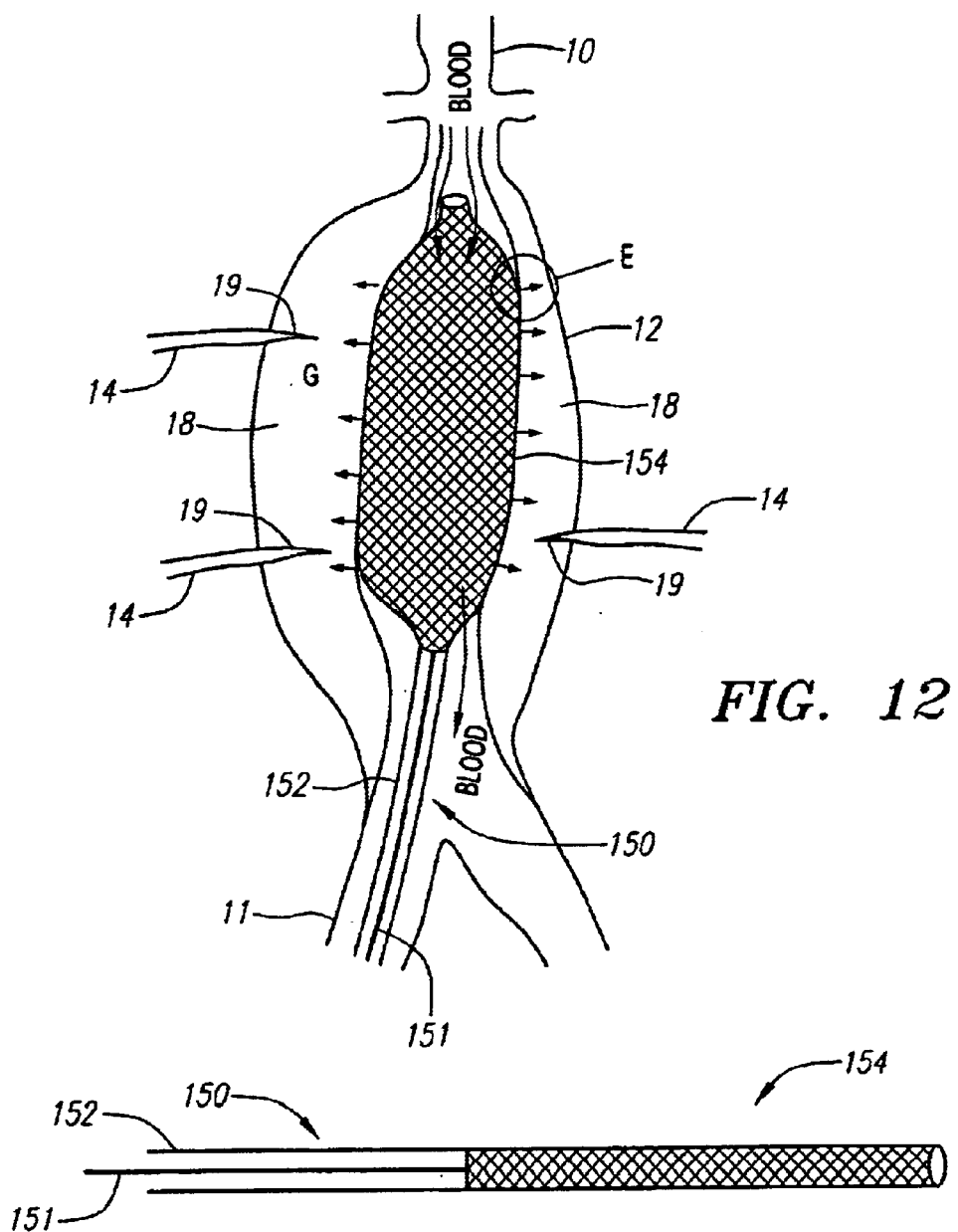
FIG. 12
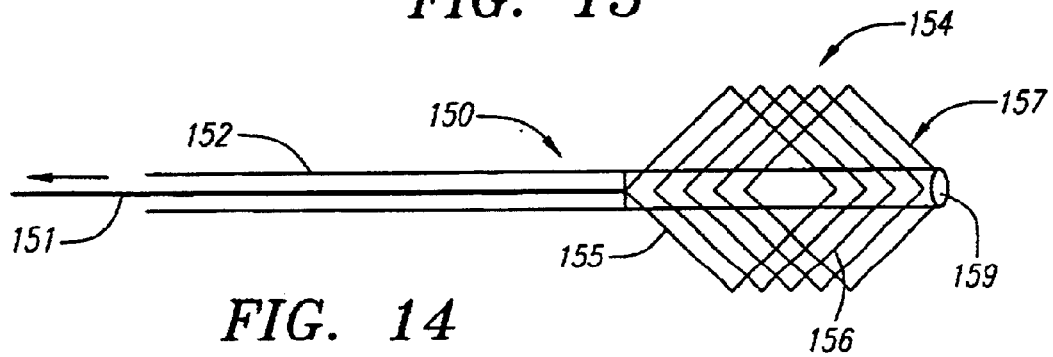
FIG. 13
FIG. 14

METHOD FOR THERMAL TREATMENT OF TYPE II ENDOLEAKS IN ARTERIAL ANEURYSMS

FIELD OF THE INVENTION

The present invention relates to endoluminal surgical procedures and devices and, more particularly, to an endoluminal method and apparatus that facilitates the prevention of type II endoleaks associated with post stent-graft treated arterial aneurysms.

BACKGROUND OF THE INVENTION

For a significant portion of the general public, abdominal aortic aneurysms (AAA) represent a major medical problem. Aneurysms are a form of atherosclerosis characterized by degeneration of the arterial wall in which the wall weakens and balloons outward by thinning. The conventional approach to repairing aneurysms involves a very invasive operation entailing the dissection of the aorta and replacement of the aneurysm with an artificial artery known as a prosthetic graft. In order to expose the aorta and perform this procedure, a significant abdominal incision extending from the breast bone to the pubic bone is required.

Over recent years, however, physicians have made widespread use of a significantly less invasive approach to aneurysmal repair involving the transluminal placement of an endoluminal graft within the aorta. With the use of expandable stents, the graft is attached to the internal surface of the arterial wall, above and below the aneurysm, without sewing. Once in place, the blood flows through the graft by-passing the aneurysm.

It has been reported, however, that about thirty percent of all aneurysms repaired with endoluminal stent-grafts fail to adequately exclude the associated aneurysmal sac from systematic aortic pressures. Eighty percent or more of these failures are said to be due to type II endoleaks. Type II endoleaks occur when blood flow takes a circuitous route traveling through branches from the non-stented portion of the aorta through anastomotic connections into collateral vessels with a direct communication with the aneurysmal sac. Blood then travels in a retrograde direction in these collateral vessels, eventually emptying into the sac behind the stent-graft. These collateral vessels, prior to aortic exclusion via the stent-graft, carried blood from the aorta to nutrient beds of lower pressure. When the aorta from which they originate is excluded, the pressure gradient favors flow in the opposite direction. In conventional surgical repairs of aneurysms, these collateral vessels are typically ligated. This is not possible with current endoluminal graft technology.

Moreover, current endoluminal graft technology does not enable a physician to stop such endoleaks once the stent-graft has been placed and the leak has formed. Although embolization has been demonstrated to occlude flow to the aneurysmal sac from embolized vessels, this approach tends to be largely ineffective. Because the aneurysmal sac provides so many paths through which blood can flow, like the "nidas" of an arterial-venous-malformation (AVM) (see FIG. 5), it is difficult to stop the flow entirely without destroying the "nidas."

Thus, it is desirable to provide a method and apparatus that facilitates the prevention or elimination of type II endoleaks in stent-graft treated aneurysmal sacs and other arterial aneurysms.

SUMMARY OF THE INVENTION

The present invention is directed to a method and apparatus that facilitates the prevention or elimination of type II endoleaks in stent-graft treated arterial aneurysms, such as aneurysms occurring in the abdominal aorta, the iliac, the thoracic aorta, and the like. In a preferred embodiment, an apparatus of the present invention comprises a perfusion balloon catheter having an elongate tubular body with a balloon mounted on the body adjacent its distal end. The balloon preferably comprises a plurality of energy conducting elements attached thereto for transmitting RF energy to tissue to be treated. Alternatively, the apparatus of the present invention may comprise a catheter having an elongate tubular body with a wire mesh basket extending from its distal end. An articulating wire attaches to the distal end of the wire basket and extends through the catheter body. When pulled, the articulating wire applies a force to the distal end of the basket to compress the basket longitudinally and expand the basket radially.

In operation, e.g., for treatment of an abdominal aorta aneurysm (AAA), the catheter is inserted into a femoral artery of a patient and then advanced through the femoral artery into the aorta until the balloon or basket is positioned within the aneurysmal sac. Once in place, the balloon or basket is expanded to compress a clot material within the aneurysmal sac and close collateral blood flow pathways through the clot material. The compression is preferably conducted under a pressure in the range of about 2–5 atmospheres. While compressed, the clot material is heated by transmitting RF energy to the wire basket or the conducting elements on the balloon until the clot material is cauterized or coagulated and collateral blood flow pathways through the clot material are occluded. Other means of heating may include inductive or direct current (DC) heating. The balloon or basket is then returned to an unexpanded state and the catheter is removed from the aorta. Once the catheter is removed, a stent-graft may be placed within the aorta in accordance with conventional endoluminal graft methodology.

Further, objects and advantages of the invention will become apparent from the following detailed description and accompanying drawings.

BRIEF DESCRIPTION OF DRAWINGS

FIG. 12 is a cut-away diagrammatic view of the abdominal aorta artery and aneurysm sac of FIG. 9 with a thermal ablation catheter of the present invention having a wire-mesh basket positioned within the aneurysm sac and expanded to treat the aneurysm sac to prevent the formation of a type II endoleak post stent-graft placement.

FIG. 13 is a diagrammatic view of the thermal ablation catheter with its wire-mesh basket in an unexpanded state.

FIG. 14 is a diagrammatic view of the thermal ablation catheter with its wire-mesh basket in an expanded state.

DETAILED DESCRIPTION OF PREFERRED EMBODIMENTS

Referring in detail to the drawings, an improved method and apparatus for preventing or eliminating type II endoleaks in arterial aneurysms is described and illustrated herein. For exemplary purposes only, the following discussion focuses on the treatment of type II endoleaks in abdominal aorta aneurysms. However, one skilled in the art will understand that the method and apparatus discussed herein may be used to treat type II endoleak of other arterial aneurysms in such arteries as the iliac, the thoracic aorta and the like.

Figure 1:
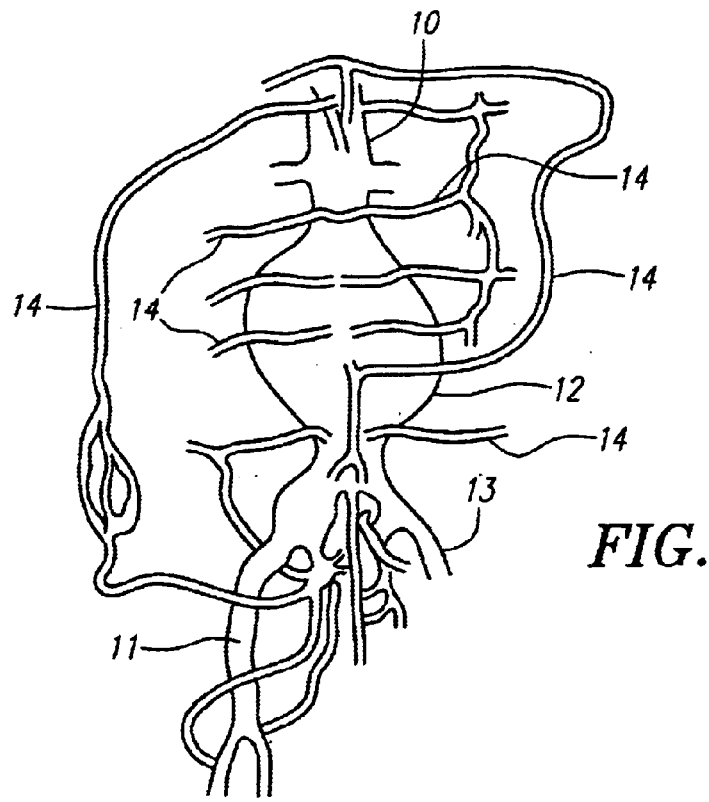
FIG. 1 is a diagrammatic view of an abdominal aorta artery with an aneurysm sac and collateral vessels.

Turning to FIG. 1, a diagrammatic view of an abdominal aorta 10 is provided. As depicted, the abdominal aorta 10 includes a section in which its walls are ballooned out forming an abdominal aortic aneurysm (AAA). As is typical, numerous collateral vessels 14 are shown to be interconnected with the aneurysmal sac 12 and/or the non-aneurysm portion of the aorta 10.

Figure 2:
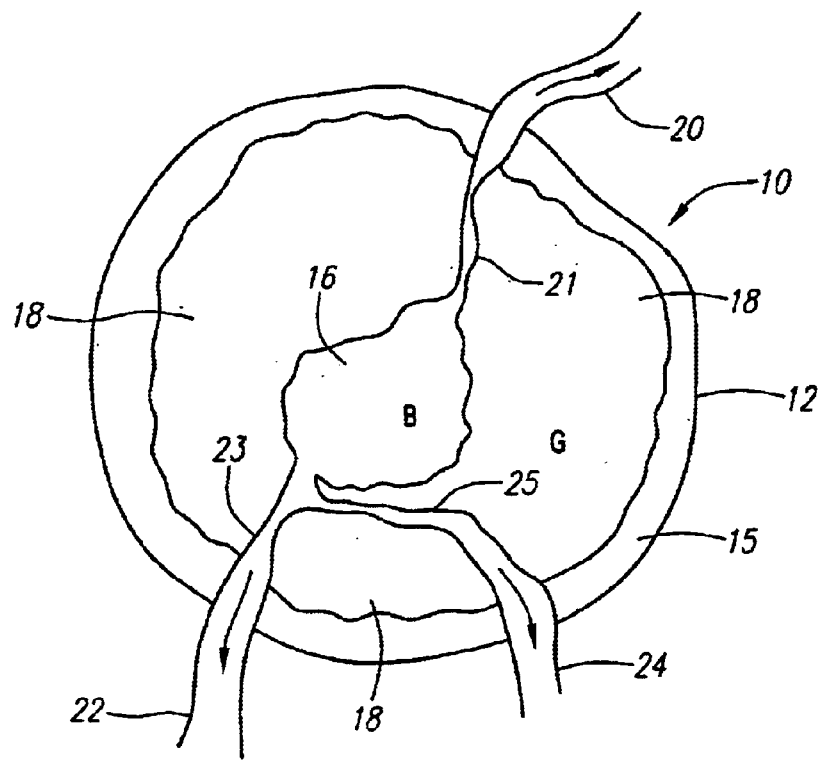
FIG. 2 is a cross-section view through an abdominal aorta aneurysm sac showing blood flow through the abdominal aorta aneurysm sac and out to the internal mammary (IMA) and lumbar arteries prior to treatment.

Referring to FIG. 2, the aneurysmal sac 12 typically includes a gelatinous clot material 18 filling the space bounded by the expanded arterial wall 15. The main blood flow from the aorta 10 to the femoral arteries 11 and 13 passes through the aneurysmal sac 12 through a channel 16 formed in the gelatinous clot material 18. As depicted, blood also flows through collateral pathways 21, 23 and 25 formed in the gelatinous clot material 18 to an internal mammary artery (IMA) 20 and a pair of lumbar arteries 22 and 24.

Figure 3:
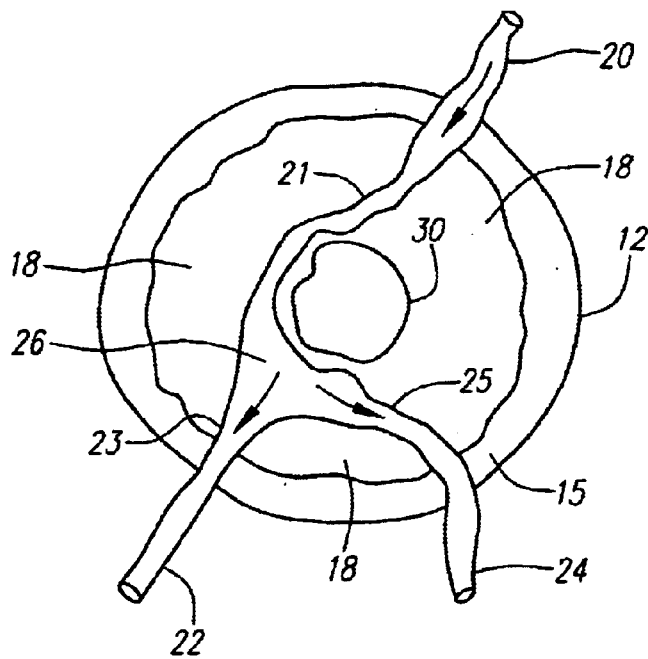
FIG. 3 is a cross-section view through an abdominal aorta aneurysm sac post stent-graft placement showing blood flow through a typical IMA to lumbar type II endoleak.
Figure 4:
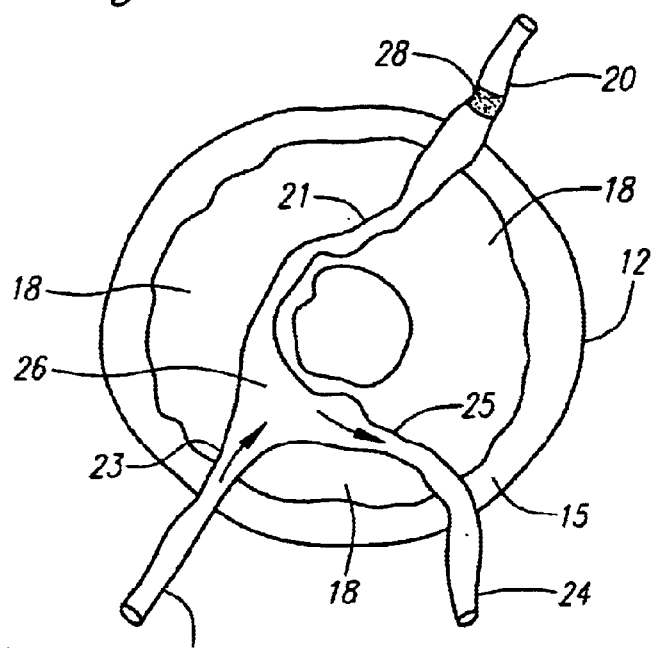
FIG. 4 is a cross-section view through an abdominal aorta aneurysm sac post stent-graft placement showing blood flow through a typical IMA to lumbar type II endoleak after IMA embolization.
Figure 5:
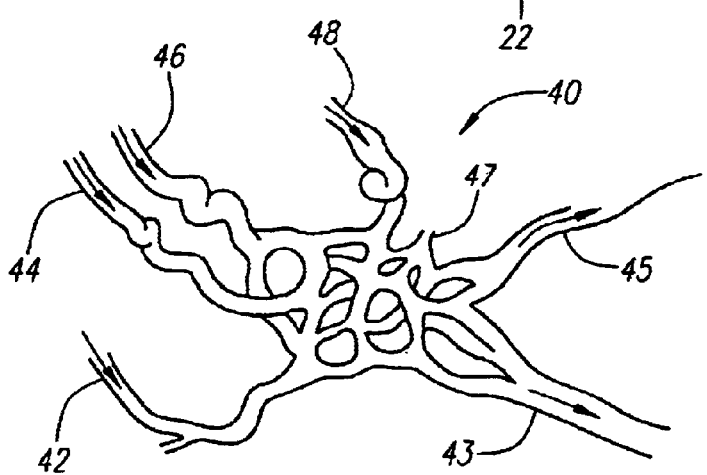
FIG. 5 is a diagrammatic view of an arterial venous malformation.

Turning to FIGS. 3 and 4, a stent-graft 30 is shown centrally placed within the aneurysmal sac 12. A typical IMA 20 to lumbar 22 and 24 type II endoleak 26 is depicted in FIG. 3 wherein blood enters from the IMA 20, fills the endoleak 26 and then exits through the lumbar vessels 22 and 24. In such leaks, the blood tends to channel in circuitous routes through the gelatinous clot material 18 passing through collateral pathways 21, 23 and 25 between the IMA 10 and the lumbar arteries 22 and 24. In FIG. 4, embolization of the IMA 20, with a coil, embolics or the like 28, is shown to be ineffective in stopping such leaks. For instance, once the IMA 20 is blocked, blood simply flows into the sac 12 from one of the lumbar arteries 22 instead of the IMA 20, fills the endoleak 26, and then exits through the other lumbar artery 24. Because the aneurysmal sac 12 tends to act like a nidas of an arterial venous malformation (AVM) 40 having multiple entering 42, 44, 46 and 48 and exiting 43, 45 and 47 pathways (see FIG. 5), it is difficult to stop the flow entirely without destroying the "nidas."

Once the stent-graft 30 has been endoluminally placed so that blood flow by-passes the aneurysmal sac 12, and an endoleak 26 has formed, current endoluminal graft technology can not enable a physician to endoluminally treat or eliminate the endoleak 26. Accordingly, the present invention is directed to a method and apparatus that tends to prevent the formation of such leaks by treating the aneurysmal sac 12 prior to endoluminal placement of the stent-graft 30.

Figure 6:
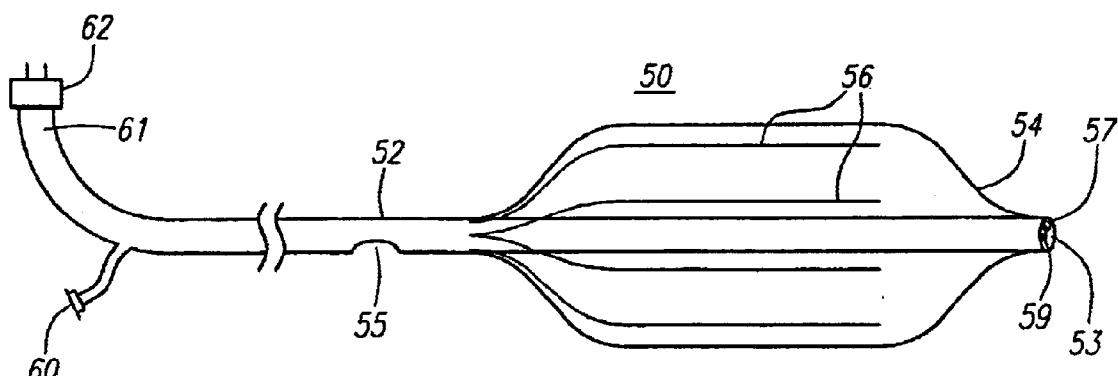
FIG. 6 is a diagrammatic view of the thermal ablation balloon catheter of the present invention.

Referring to FIG. 6, an illustrated embodiment of a perfusion-type balloon catheter 50 of the present invention is shown to include an elongate tubular body 52 having proximal and distal ends and a balloon 54 attached to the body 52 adjacent its distal end. The balloon 54 is shown in an operative or expanded state. However, one of skill in the art would understand that the balloon 54 may be rolled or folded about the catheter body 52 to create a low profile for insertion of the catheter 50 into a patient.

The catheter body 52 is preferably formed from a semi-compliant material to enable the catheter 50 to easily pass through a vessel or artery, such as the femoral artery, and make its way into the interior regions of a patient's aorta 10. The body 52, which is open at its distal end, includes at least three lumens—a main or perfusion lumen 53, a guidewire lumen 57 and a fill/evacuate lumen 59. A hole (not shown) in the wall of the catheter body 52 enables the fill/evacuate lumen 59 to communicate with the interior of the balloon 54. The guidewire lumen 57 generally extends the length of the body 52. The perfusion lumen 53 extends from the axial opening at the distal end of the body 52 to a radial perfusion opening 55 extending longitudinally in the wall of the body 52 just beyond where a proximal end of the balloon 54 attaches to the body 52. The perfusion catheter 50 may also be in the form shown in U.S. Pat. Nos. 5,458,579, 5,087,247, or 4,581,017, the disclosures of which are incorporated herein by reference.

Figure 6A:
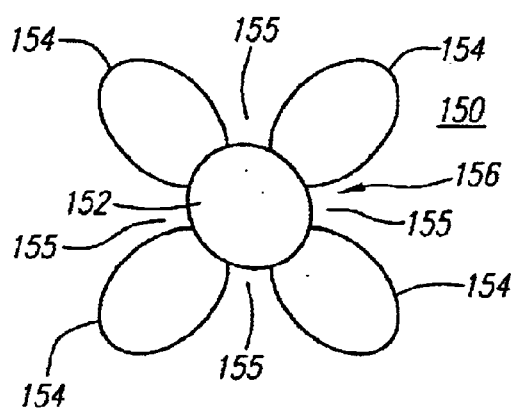
FIG. 6A is a diagrammatic end view of an alternative embodiment for a balloon catheter of the present invention.

The perfusion catheter 150 may include a multi-lobular balloon 156 as shown in FIG. 6A. Individual balloon lobes 154 are attached to the catheter body 152 and, when inflated, form gaps 155 therebetween. Instead of passing through a catheter lumen, blood passes through the gaps 155 between the balloon lobes 154.

The balloon 54 is generally cylindrical in shape and is preferably formed from compliant or semi-compliant material to minimize risk of rupture and to enable conformability within the aneurysmal sac 12. RF conductive elements 56, such as metallic wire or circuit traces, are attached to the outer surface of the balloon 54 and are used to transmit energy to tissue such as the gelatinous clot material 18 in a monopolar or bipolar manner. A wire (not shown) for providing power to the wire traces 56 on the balloon 54 may extend as a trace along the body 52 or may be encapsulated in the body 52 of the body. The wire preferably connects to an electrical cable 61 that extends from the proximal end of the body 52 of the catheter 50. The cable 61 ends with a plug 62 that connects with an energy source and appropriate conventional catheter control equipment (not shown). Preferably, the energy source is capable of supplying power in a range of about 20–200 watts.

Figure 7:
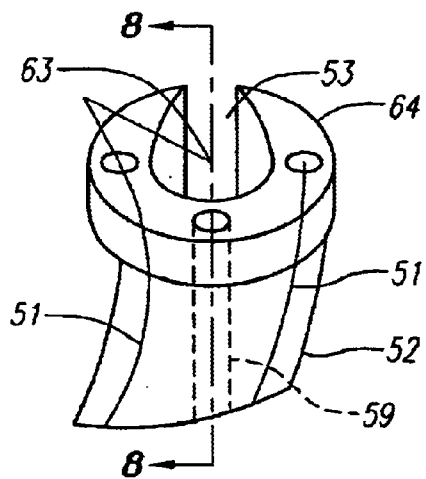
FIG. 7 is a detailed partial view of a distal tip of the thermal ablation balloon catheter shown in FIG. 9.
Figure 7A:
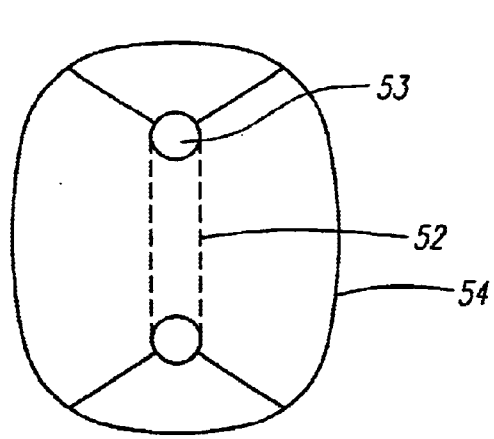
FIG. 7A is a diagrammatic view of a balloon attached to the distal tip shown in FIG. 7.
Figure 8:
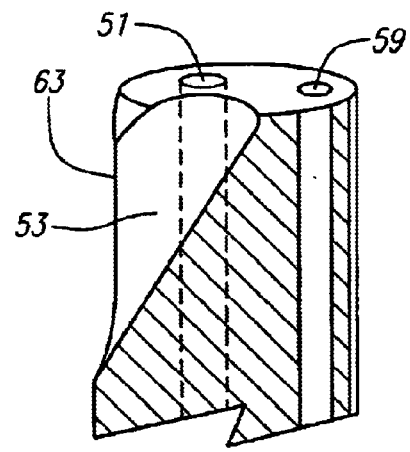
FIG. 8 is a cross-sectional view of the distal tip of the thermal ablation balloon catheter taken along line 8—8 of FIG. 7.

As shown in FIGS. 6, 7 and 8, the body 52 also includes a fill/evacuate lumen 59 and a fill/evacuate port 60 extending from catheter body 52 toward its proximal end. Multiple wire lumens 51 may also be provided as shown. In addition, the distal end of the catheter body 52 may include a conically shaped slit 63 forming a radially directed and longitudinally extending opening into the perfusion lumen 53 to improve blood flow into the perfusion lumen 53. With the slit 63, the distal tip 64 of the catheter body tends to have a semi-annular or horse-shoe like shape. As shown in FIG. 7A, the balloon 54 may be attached to the distal tip 64 and have an inflated shape that directs blood flow toward the slit 63 and into the lumen 53.

Figure 9:
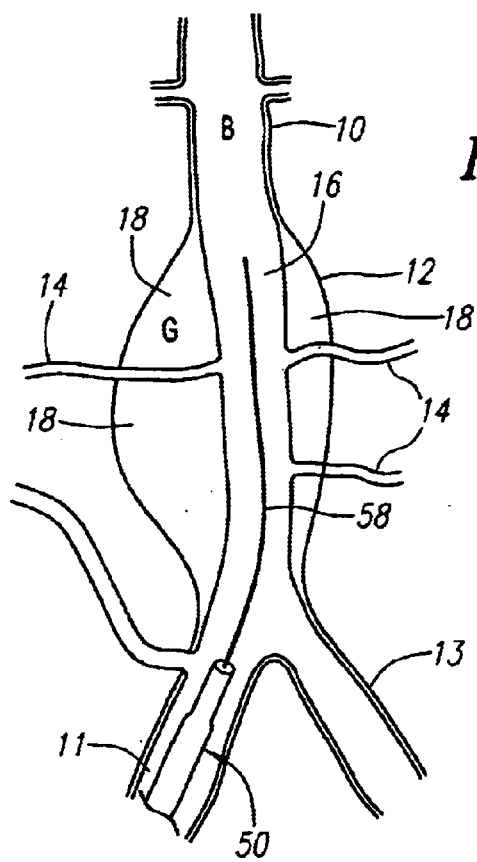
FIG. 9 is a cut-away diagrammatic view of an abdominal aorta artery with an aneurysm sac and collateral vessels.
Figure 10:
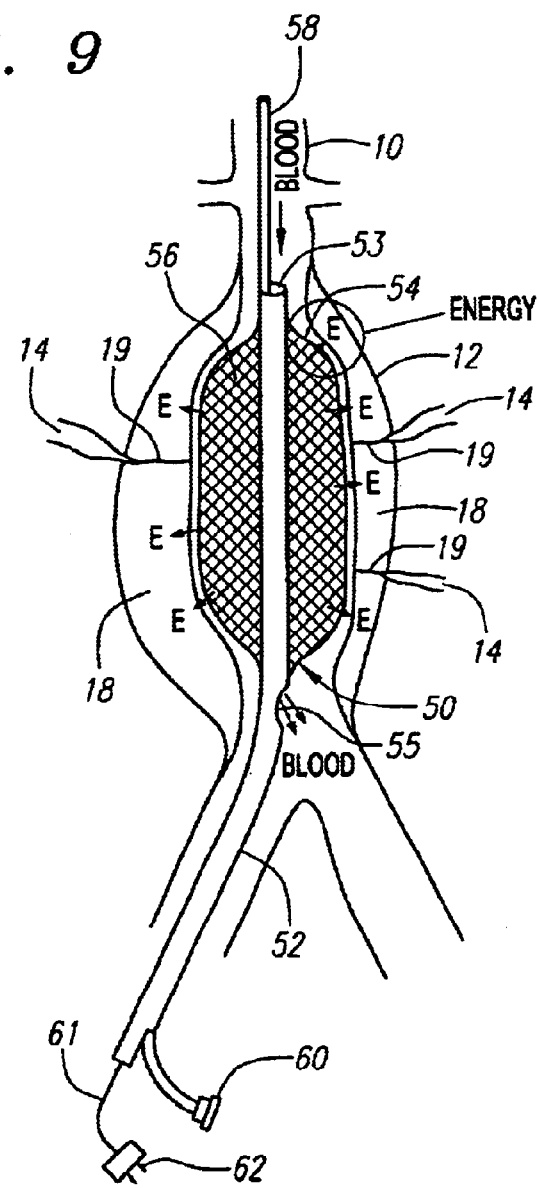
FIG. 10 is a cut-away diagrammatic view of the abdominal aorta artery and aneurysm sac of FIG. 9 with a thermal ablation balloon catheter of the present invention positioned within the aneurysm sac and expanded to treat the aneurysm sac to prevent the formation of a type II endoleak post stent-graft placement.

As noted above, the catheter 50 of the present invention is preferably used to treat the gelatinous clot material 18 of the aneurysmal sac 12 prior to placement of the stent-graft 30. In operation, as shown in FIGS. 9 and 10, the catheter 50, with the balloon 54 in an uninflated state, is inserted into one of the femoral arteries 11 in the groin region of the patient. The catheter 50 is then guided through the femoral artery 11 into the abdominal aortic artery 10 along a guidewire 58. The catheter 50 is positioned within the aorta 10 such that the balloon 54 of the catheter is positioned within the aneurysmal sac 12 using well known visualization techniques such as x-ray, ultrasound, and the like.

Once in position, the balloon 54 is inflated with about 2–5 atmospheres of pressure, such that the gelatinous clot material 18 is compressed. With the balloon 54 inflated, blood flow through the aorta 10 is occluded and must flow through the perfusion lumen 53 of the catheter 50. Blood flow enters the perfusion lumen 53 through the opening in the distal end of the catheter body 52 and the conically shaped slit 63. After passing through the perfusion lumen 53, blood flows out of the perfusion opening 55 toward the proximal end of the catheter body 52 into the lower aorta 10 and femoral arteries 11 and 13. If the balloon catheter 150 shown in FIG. 6A is used, the blood would flow through the gaps 155 between the balloon lobes 156.

With the clot material 18 compressed or condensed, flow through the collateral pathways 19 is blocked. RF energy is then transmitted to the conductive elements 56 on the exterior of the balloon 54. As shown, the energy E is directed from the elements 56 on the balloon 54 into the clot material 18 in the aneurysmal sac 12. Alternatively, heating may be accomplished inductively or with DC. Depending on the size of the lesion and the heat transfer parameters of the gelatinous clot material 18, energy may be applied in a power range of about 20–200 watts. The heat tends to cauterize or coagulate the clot material 18. Optionally, the clot material 18 may be cauterized by rapidly pulsing the RF energy E into the clot material 18 to a depth of about 1–2 mm. The heating of blood is preferably minimized to the point of coagulation of the blood or other non-target tissue to avoid creating distal embolisms and/or other unnecessary vessel injury responses.

Figure 11:
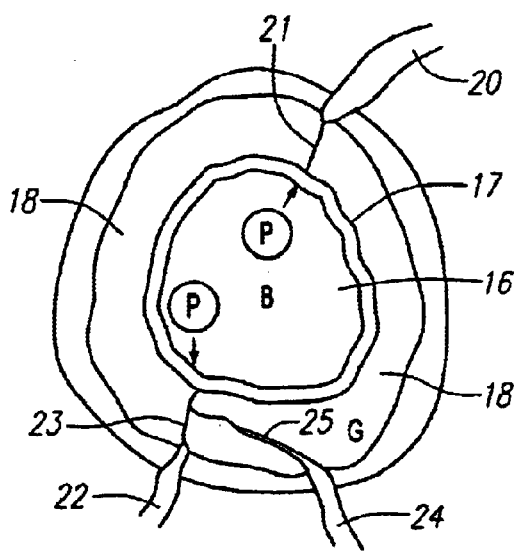
FIG. 11 is a cross-sectional view through the abdominal aorta aneurysm sac post treatment with the thermal ablation balloon catheter of the present invention.

The cauterized tissue tends to form an inner egg shell layer 17, occluding or blocking collateral pathways 19 formed in the clot material 18 that had connected the collateral arteries 14. As shown in FIG. 11, the collateral pathways 21, 23 and 25 through the clot material 18 are blocked, thus preventing the channeling of blood through the clot material 18 between the IMA 20 and lumbar arteries 22 and 24. The cauterized tissue tends to scar over time and form a permanent occlusion such that no new collateral pathways may form within the clot 18.

After deflation of the balloon 54 and removal of the catheter 50 from the aneurysmal sac 12, the stent-graft 30 may be installed in a routine manner in accordance with conventional procedures.

Turning to FIGS. 12–14, an alternate embodiment of the present invention is shown to comprise a catheter 150 having an elongate tubular body 152 with distal and proximal ends. An expandable wire mesh basket 154 extends from the distal end of the catheter body 152 and a cable (not shown) extends from the proximal end of the catheter body 152. The cable includes a plug (not shown) that connects with an energy source and conventional catheter control equipment (not shown).

The wire basket 154, as shown in FIG. 13, includes a mesh of criss-crossing wires that are uninsulated at a midsection 156 of the basket 154 and insulated at proximal and distal end portions 155 and 157 of the basket 154. The basket 154 may include a membrane such as a braided fabric to prevent the basket 154 from slicing or cutting into the gelatinous clot material 18 too deeply such that the basket becomes lodged or creates emboli upon removal.

An articulating wire 151 extends through the interior of the catheter body 152 and basket 154 to a ring attached to the distal end of the basket 154. When the articulating wire 151 is withdrawn from or pulled out of the catheter body 152, the corresponding force applied to the distal end of the basket 154 causes the basket 154 to longitudinally compress and radially expand. (See FIG. 13). When the articulating wire 151 is released, the basket 154 returns in spring-like fashion to its unexpanded, low profile state.

In operation, the catheter 150, with the basket 154 in an unexpanded state, is inserted into one of the femoral arteries 11 in the groin region of the patient. The catheter 150 is then guided through the femoral artery 11 into the abdominal aorta 10 along a guidewire (not shown). The catheter 150 is positioned within the aortic artery 10 such that the basket 154 of the catheter 150 is positioned within the aneurysmal sac 12. Once in position, as shown in FIG. 12, the basket 154 is expanded by drawing or pulling on the articulating wire 151 such that the gelatinous clot material 18 is compressed. With the basket 154 expanded, blood flow through the aorta 10 flows through the basket 154 into the lower aorta 10 and femoral arteries 11 and 13.

With the clot material 18 compressed or condensed, flow through the collateral pathways 19 is blocked. RF energy is then transmitted to the basket 154. As shown, the energy E is directed from the basket 154 into the clot material 18 in the aneurysmal sac 12. Depending on the size of the lesion and the heat transfer parameters of the gelatinous clot material 18, energy may be applied in a range of about 20-200 watts. The heat tends to cauterize the clot material 18. As with the previous embodiment, the heating of blood is preferably minimized to the point of coagulation of the blood or other non-target tissue to avoid creating distal embolisms and/or other unnecessary vessel injury responses.

After the basket 154 is returned to its unexpanded state and the catheter 150 is removed from the aneurysmal sac 12, the stent-graft 30 may be installed in a routine manner in accordance with conventional procedures.

While various preferred embodiments of the invention have been shown for purposes of illustration, it will be understood that those skilled in the art may make modifications thereof without departing from the true scope of the invention as set forth in the appended claims including equivalents thereof.

What is claimed:

1. A method for treating an aneurysmal sac with a catheter having a wire basket and an articulating wire extending from a distal end of the wire basket, comprising:

introducing the wire basket into the aneurysmal sac;

pulling the articulating wire to longitudinally compress the wire basket, wherein the wire basket is radially expanded to compress a clot material within the aneurysmal sac, and heating the compressed clot material.

2. The method of claim 1 wherein the clot material is cauterized by the heating step.

3. The method of claim 1 wherein the clot material is compressed under about two to five atmospheres of pressure.

4. The method of claim 1 wherein the compressed clot material is heated by transmitting RF energy to the clot material.

5. The method of claim 4 wherein the RF energy is transmitted to the clot material via the wire basket.

6. The method of claim 1, wherein the clot material is heated by transmitting heat through the wire basket.

7. The method of claim 1, further comprising percutaneously introducing the catheter through a blood vessel.

8. The method of claim 1, wherein the aneursymal sac is located in the abdominal aorta.

9. The method of claim 1, further comprising installing a stent-graft along the inner surface of the aneurysmal sac.

10. A method for treating an aneurysmal sac, comprising:
    compressing a clot material within the aneurysmal sac;
    heating the compressed clot material; and
    installing a stent-graft along the inner surface of the aneurysmal sac.

11. The method of claim 10 wherein the clot material is cauterized by the heating step.

12. The method of claim 10 wherein the clot material is compressed under about two to five atmospheres of pressure.

13. The method of claim 10 wherein the compressed clot material is heated by transmitting RF energy to the clot material.

14. The method of claim 10 wherein the aneursymal sac is located in the abdominal aorta.

15. A method for preventing type II endoleaks within an aneurysmal sac, the aneurysmal sac containing a clot material with collateral pathways, the method comprising:
    compressing the clot material, wherein the blood flow through the collateral pathways is blocked;
    heating the compressed clot material; and
    installing a stent-graft along the inner surface of the aneurysmal sac.

16. The method of claim 15 wherein the clot material is cauterized by the heating step.

17. The method of claim 15 wherein the clot material is compressed under about two to five atmospheres of pressure.

18. The method of claim 15 wherein the compressed clot material is heated by transmitting RF energy to the clot material.

19. The method of claim 15 wherein the aneursymal sac is located in the abdominal aorta.

* * * * *